United States Patent
Cormier et al.

(10) Patent No.: US 9,823,225 B2
(45) Date of Patent: *Nov. 21, 2017

(54) INJECTOR SAMPLE DILUTION FOR A LIQUID CHROMATOGRAPHY SYSTEM

(71) Applicant: Waters Technologies Corporation, Milford, MA (US)

(72) Inventors: Sylvain Cormier, Mendon, MA (US); Mark W. Moeller, Norton, MA (US); Peyton C. Beals, Wrentham, MA (US)

(73) Assignee: WATERS TECHNOLOGIES CORPORATION, Milford, MA (US)

(*) Notice: Subject to any disclaimer, the term of this patent is extended or adjusted under 35 U.S.C. 154(b) by 86 days.

This patent is subject to a terminal disclaimer.

(21) Appl. No.: 14/824,431

(22) Filed: Aug. 12, 2015

(65) Prior Publication Data

US 2016/0054274 A1 Feb. 25, 2016

Related U.S. Application Data

(60) Provisional application No. 62/041,199, filed on Aug. 25, 2014.

(51) Int. Cl.
*G01N 30/20* (2006.01)
*G01N 30/06* (2006.01)
(Continued)

(52) U.S. Cl.
CPC .............. *G01N 30/20* (2013.01); *G01N 30/06* (2013.01); *G01N 30/24* (2013.01);
(Continued)

(58) Field of Classification Search
CPC ........ G01N 30/06; G01N 30/20; G01N 30/24; G01N 2030/201; G01N 2030/202; G01N 2030/207
(Continued)

(56) References Cited

U.S. PATENT DOCUMENTS 4,036,063 A * 7/1977 Roof .................. G01N 1/38
137/897
6,790,361 B2 9/2004 Wheat et al.
(Continued)

FOREIGN PATENT DOCUMENTS

WO 2009111229 A2 9/2009
WO 2014076521 A1 5/2014

OTHER PUBLICATIONS

Extended Search Report in related European Patent Application No. 15182121.2, dated Jan. 18, 2016; 7 pages.

*Primary Examiner* — Natalie Huls
*Assistant Examiner* — Monica S Young
(74) *Attorney, Agent, or Firm* — Schmeiser, Olsen & Watts LLP; William G. Guerin

(57) ABSTRACT

Described are a method and a system for diluting a sample at a location of injection in a liquid chromatography system. The method includes loading a sample into a first fluid channel, separating a flow of a mobile phase into a first flow in the first fluid channel and a second flow in a second fluid channel, and combining the sample that is displaced from the first fluid channel and the mobile phase exiting the second fluid channel at the location of injection into the system flow to thereby generate a diluted sample in the system flow. The dilution ratio of the diluted sample is responsive to the flow rates of the first and second flows. Advantageously, the flow rates can be changed by changing the flow restriction of one of the fluid channels. Thus providing the proper flow restriction enables a user to obtain a desired dilution ratio.

14 Claims, 9 Drawing Sheets

(51) Int. Cl.
*G01N 30/02* (2006.01)
*G01N 30/24* (2006.01)

(52) U.S. Cl.
CPC . *G01N 2030/027* (2013.01); *G01N 2030/201* (2013.01); *G01N 2030/202* (2013.01); *G01N 2030/207* (2013.01)

(58) Field of Classification Search
USPC ........................................................ 73/61.55
See application file for complete search history.

(56) References Cited

U.S. PATENT DOCUMENTS

| | | | |
|---|---|---|---|
| 7,875,175 B2 | 1/2011 | Wheat et al. | |
| 7,909,994 B2 | 3/2011 | Wheat et al. | |
| 8,642,351 B2 * | 2/2014 | Liu | G01N 30/34 210/198.2 |
| 2003/0223913 A1 * | 12/2003 | Karp | G01N 30/16 422/400 |
| 2011/0016955 A1 * | 1/2011 | Cormier | G01N 1/38 73/61.55 |
| 2012/0103075 A1 * | 5/2012 | Cormier | F04B 13/02 73/61.55 |
| 2012/0305464 A1 | 12/2012 | Cormier | |
| 2015/0316455 A1 * | 11/2015 | Anderer | B01F 3/0865 73/61.55 |

* cited by examiner

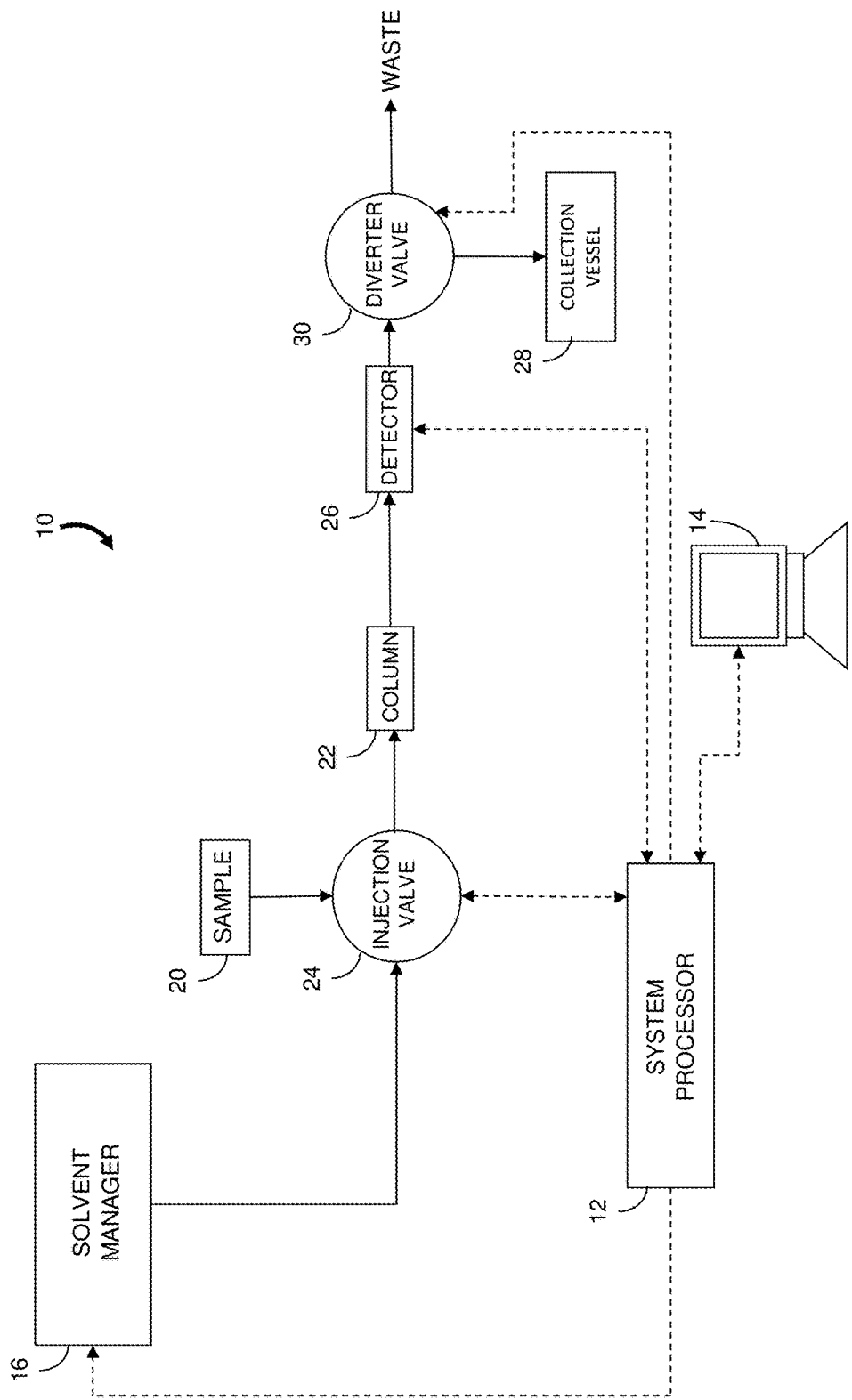

INJECTOR SAMPLE DILUTION FOR A LIQUID CHROMATOGRAPHY SYSTEM

RELATED APPLICATION

This application claims the benefit of the earlier filing date of U.S. Provisional Patent Application No. 62/041,199, filed Aug. 25, 2014 and titled "Injector Sample Dilution for a Liquid Chromatography System," the entirety of which is incorporated herein by reference.

FIELD OF THE INVENTION

The invention relates generally to liquid chromatography systems. More particularly, the invention relates to a method for diluting a sample during injection of the sample into a mobile phase.

BACKGROUND

High pressure liquid chromatography (HPLC) systems sometimes require the dilution of a sample before the sample is injected into the mobile phase flowing to a chromatography column. For example, the sample may be dissolved in a strong solvent that may interact with the mobile phase and negatively affect chromatography. Normally, it is desirable to focus the sample at the head of the chromatographic column; however, strong solvents can prevent at least some of the sample from being retained at the head of the column.

Sample dilution can be performed manually by a skilled technician; however, it is not always practical for a technician to be available. In many instances, the technician and equipment for performing dilutions are located at an inconvenient distance from the HPLC system, resulting in significant delay. Moreover, there exist the risks of contamination and human error in the dilution process. In addition, the additional inconvenience of tracking transported samples is often necessary.

SUMMARY

In one aspect, a method of diluting a sample in a liquid chromatography system includes loading a sample into a first fluid channel. A flow of a mobile phase of a liquid chromatography system is separated into a first flow in the first fluid channel and a second flow in a second fluid channel. The first flow and the second flow have a first flow rate and a second flow rate, respectively. The flow of mobile phase in the first fluid channel displaces the sample in the first fluid channel. The sample exiting the first fluid channel and the mobile phase exiting the second fluid channel are combined at a location of injection into the system flow to thereby generate a diluted sample in the system flow. A dilution ratio of the diluted sample is responsive to the first flow rate and the second flow rate.

In another aspect, a system for injecting a diluted sample in a liquid chromatography system includes a first fluid channel having a first end and a second end, a second fluid channel having a first end and a second end, an injection valve and a control module. The injection valve has a first node and a second node in communication with the first end and the second end, respectively, of the second fluid channel. The injection valve has a third node configured for communication with a sample syringe. The first node is configured to receive a mobile phase of a liquid chromatography system. The control module is in communication with the injection valve to control a state of the injection valve. When the injection valve is in a first state, the third node is in communication with the first end of the first fluid channel to thereby enable a sample in a sample source in communication with the second end of the first fluid channel to be loaded into the first fluid channel. When the injection valve is in a second state, the first node is in further communication with the first end of the first fluid channel and the second node is in further communication with the second end of the first fluid channel so that the mobile phase flows into the first fluid channel and the second fluid channel, at a first flow rate and a second flow rate, respectively. The sample displaced out from the second end of the first fluid channel and the mobile phase exiting the second end of the second fluid channel are combined at the second node to generate a diluted sample having a dilution ratio that is responsive to the first flow rate and the second flow rate.

BRIEF DESCRIPTION OF THE DRAWINGS

The above and further advantages of this invention may be better understood by referring to the following description in conjunction with the accompanying drawings, in which like reference numerals indicate like elements and features in the various figures. For clarity, not every element may be labeled in every figure. The drawings are not necessarily to scale, emphasis instead being placed upon illustrating the principles of the invention.

FIG. 1 is a block diagram of a liquid chromatography system that can be used to practice embodiments of the method of the invention.

DETAILED DESCRIPTION

Figure 2A:
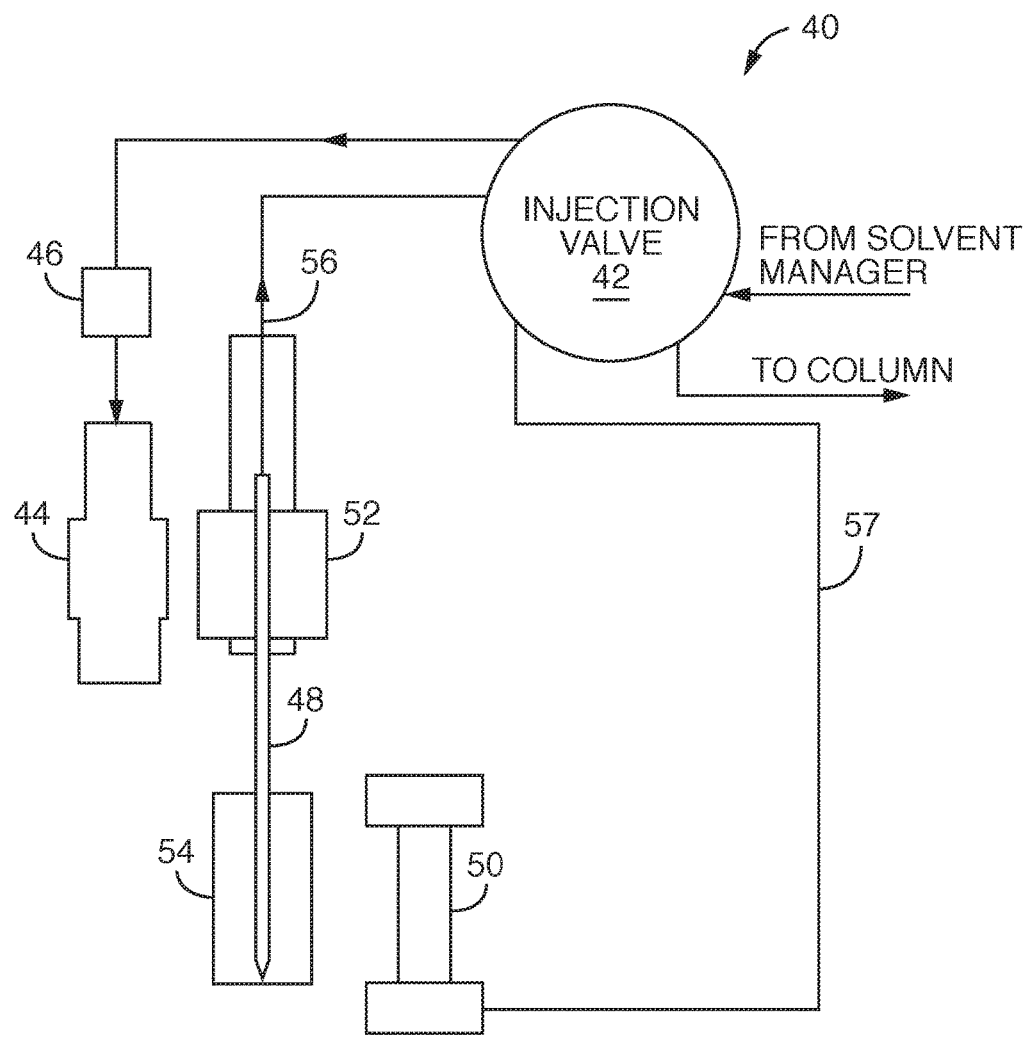
FIG. 2A is a block diagram of a system for injecting a diluted sample in a liquid chromatography system according to an embodiment of the invention and is shown in a load sample configuration.

Reference in the specification to "one embodiment" or "an embodiment" means that a particular, feature, structure or characteristic described in connection with the embodiment is included in at least one embodiment of the teaching. References to a particular embodiment within the specification do not necessarily all refer to the same embodiment.

In brief overview, the invention relates to a method and a system for diluting a sample at a location of injection in a liquid chromatography system. The method includes loading a sample into a first fluid channel, separating a flow of a mobile phase into a first flow in the first fluid channel and a second flow in a second fluid channel, and combining the sample that is displaced from the first fluid channel and the mobile phase exiting the second fluid channel at the location of injection into the system flow. The combination of the flows creates a diluted sample in the system flow. The dilution ratio is determined from the flow rates of the first and second flows. By changing the flow restriction of one of the fluid channels, the dilution ratio can be changed. A user can provide a particular flow restriction to obtain a corresponding dilution ratio.

Embodiments of the system allow for controlled dilution of a sample at the location of injection into a pressurized system flow. These embodiments can be used to replace systems that rely on the use of three valves, a needle, a needle drive, a sample syringe and a seal pact to perform similar types of injections. Advantageously, the capability to change the flow rates of the two flows can be provided at the front of a liquid chromatography system to enable an operator to easily select the desired dilution ratio. One important advantage is the range of dilution that can be realized. The user can reduce or minimize the dilution to ensure a tight injection band. Alternatively, a large dilution ratio can be used. For example, a large dilution ratio may be preferred when the sample is provided in a strong solvent that would otherwise negatively affect sample retention at the head of the chromatographic column.

The present teaching will now be described in more detail with reference to embodiments thereof as shown in the accompanying drawings. While the present teaching is described in conjunction with various embodiments and examples, it is not intended that the present teaching be limited to such embodiments. On the contrary, the present teaching encompasses various alternatives, modifications and equivalents, as will be appreciated by those of skill in the art. Those of ordinary skill having access to the teaching herein will recognize additional implementations, modifications and embodiments, as well as other fields of use, which are within the scope of the present disclosure.

FIG. 1 is a block diagram of a liquid chromatography system 10 that can be used to practice embodiments of the method of the invention. The system 10 includes a system processor 12 (e.g., microprocessor and controller) in communication with a user interface device 14 for receiving input parameters and displaying system information to an operator. The system processor 12 communicates with a solvent manager 16 which provides one or more solvents for a mobile phase. For example, the solvent manager 16 may provide a gradient mobile phase. A sample from a sample source 20 is injected into the mobile phase upstream from a chromatographic column 22 at an injection valve 24. The sample source 20 can be a sample reservoir such as a vial or other container that holds a volume of the sample. In some instances, the sample source 20 provides a diluted sample that includes the sample and a diluent. The chromatographic column 22 is coupled to a detector 26 which provides a signal to the system processor 12 that is responsive to various components detected in the eluent from the column 22. After passing through the detector 26, the system flow exits to a waste port; however, when used for fraction collection, a diverter valve 30 is used to direct the system flow to one or more collection vessels 28.

Figure 2B:
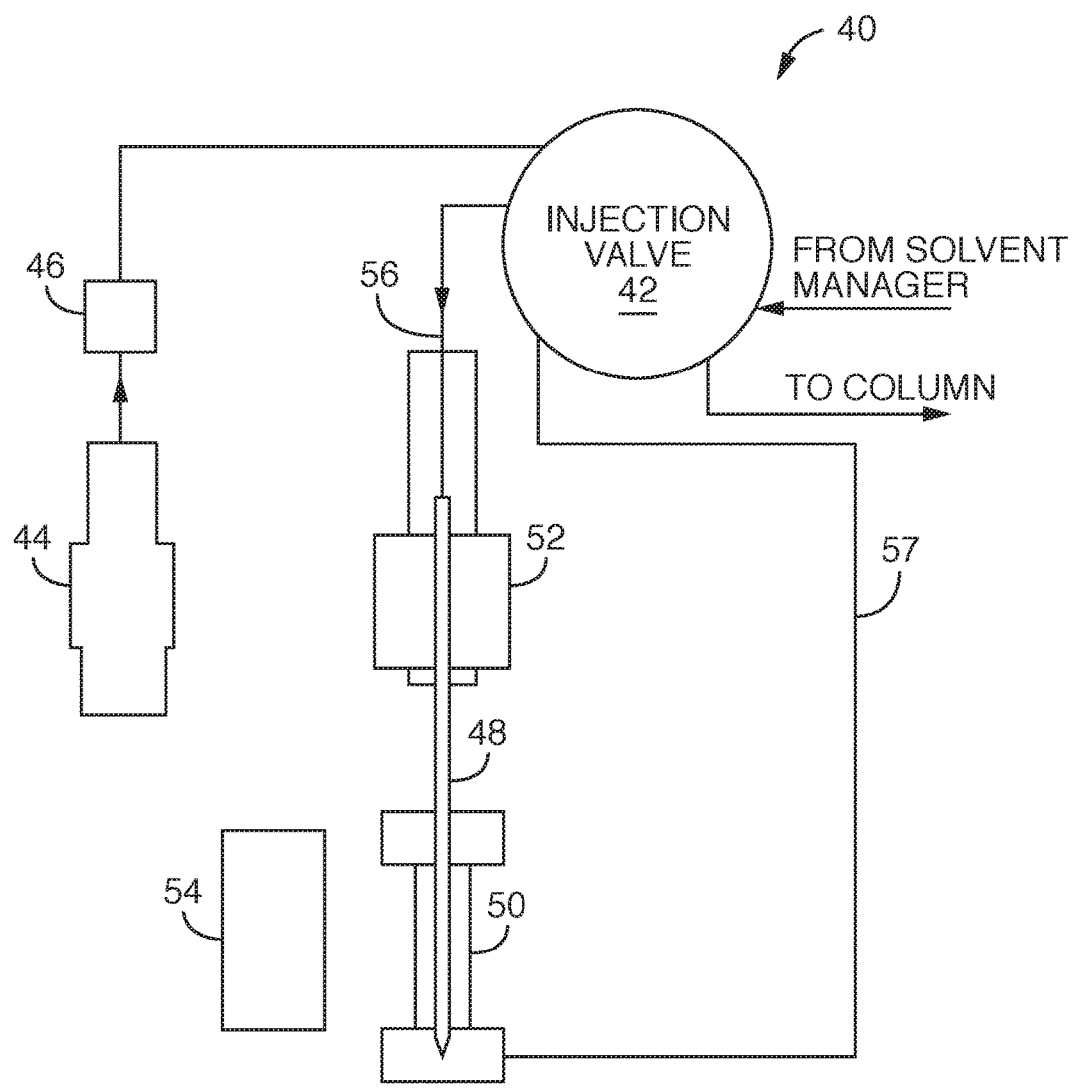
FIG. 2B is a block diagram of the system shown in FIG. 2A when configured for injecting the diluted sample.

FIG. 2A is a block diagram of a system 40 for injecting a diluted sample in a liquid chromatography system according to an embodiment of the invention. The system 40 includes an injection valve 42 that includes a number of ports each in fluidic communication with a system component, including a sample syringe 44, transducer 46, sample needle 48 and injection port 50. The injection valve 42 also includes a pair of ports to receive a mobile phase from a solvent manager and to provide the mobile phase or a diluted sample to a chromatographic column. Control of the injection valve 42 is performed using a control module (not shown) such as the system processor 12 of FIG. 1 or a valve controller in communication with the system processor 12. The system 40 further includes a needle drive 52 which is used to move the sample needle 48 to various locations. For example, the needle drive 52 is used to move the sample needle 48 into position in the sample source 54 (e.g., sample reservoir or sample vial), as illustrated, and can be used to move the sample needle 48 to a position at which the sample needle 48 engages the injection port 52 as shown in FIG. 2B. Fluidic communication between components is achieved using tubing, conduit or other structures having a fluidic channel.

Figure 3:
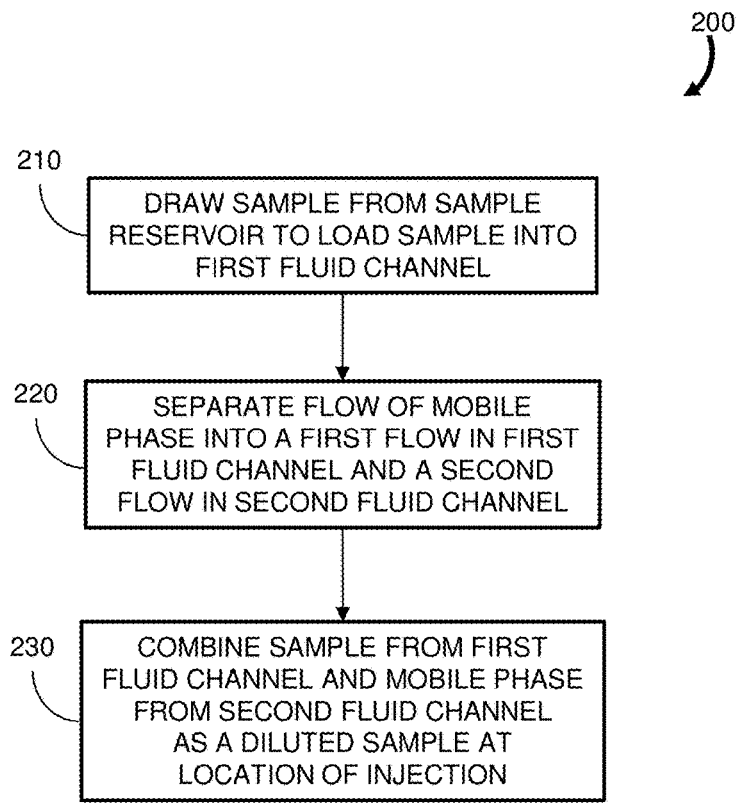
FIG. 3 is a flowchart representation of a method of diluting a sample in a liquid chromatography system according to an embodiment of the invention.
Figure 4A:
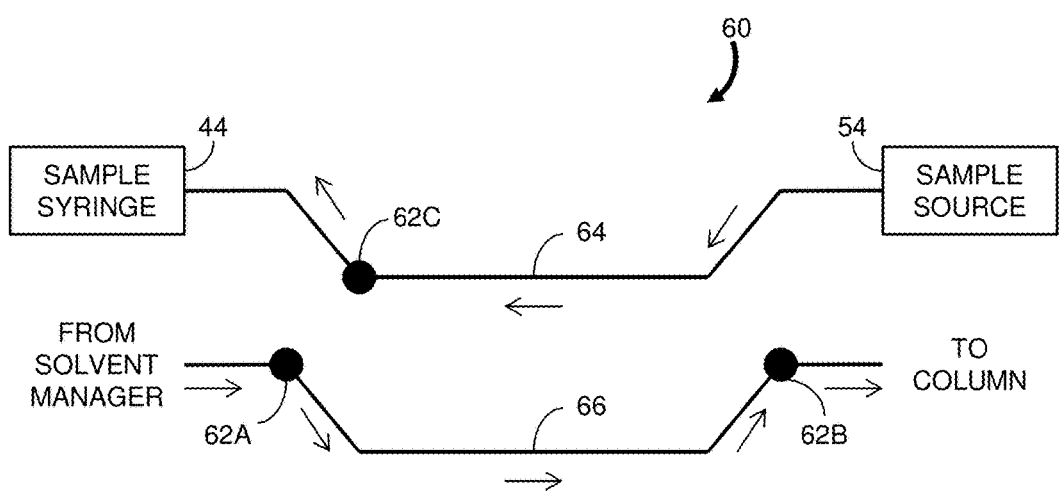
FIG. 4A and FIG. 4B are functional diagrams depicting fluid channels and nodes in an embodiment of a generalized system for injecting a diluted sample in a liquid chromatography system for an injection valve configured in a first state and a second state, respectively.
Figure 4B:
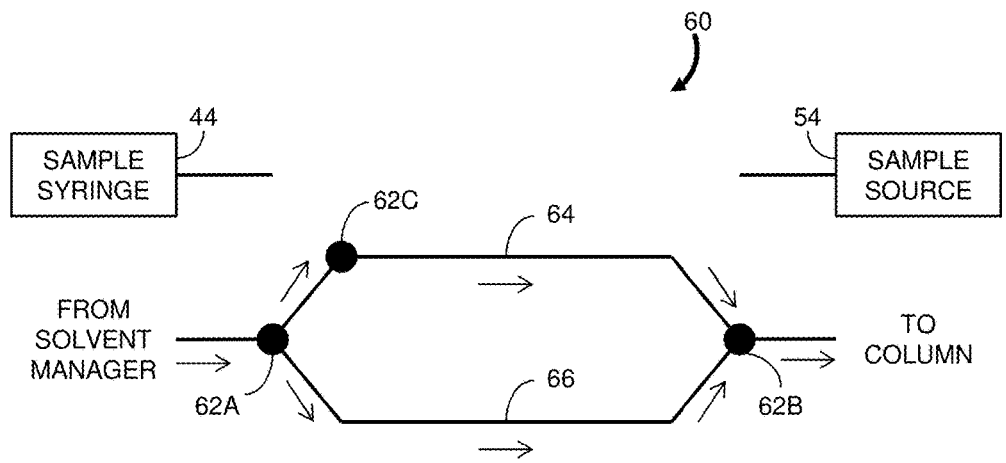

FIG. 3 is a flowchart representation of a method 200 of diluting a sample in a liquid chromatography system according to an embodiment of the invention. FIGS. 4A and 4B are functional diagrams depicting the fluidic communication paths and nodes in a generalized system 60 for injecting a diluted sample in a liquid chromatography system according to various embodiments of the invention. FIG. 4A corresponds to the system 60 configured according to an injection valve (not shown) having nodes 62A to 62C and being in a first state as shown, for example, in FIG. 2A. As used herein, a "node" means a single port on the injection valve or a plurality of ports which are in communication with each other through one or more short fluidic paths inside the injection valve. For example, the injection valve may be a rotary shear seal valve having one or more grooves in the rotor and/or stator to internally conduct fluid between ports.

One end of a first fluid channel 64 is in communication with the sample source 54 and the other end is in fixed communication with the sample syringe 44 through a node 62C. By way of example, the first fluid channel 64 can include the fluid path defined by the sample needle 48 and the tubing or conduit 56 that couples the sample needle 48 to the injection valve 42 (see FIG. 2A) so that the sample may also be drawn into a portion of the tubing 56. The system 60 also includes a second fluid channel 66 having one end in communication with a solvent manager through node 62A to receive a mobile phase and the other end in communication with a chromatographic column through node 62B.

While the injection valve is in the first state, the sample syringe 44 draws a volume of sample from the sample source 54 into the sample needle 48 during a portion of the syringe intake stroke to load (step 210) the sample into at least a portion of the first fluid channel 64. Depending on the desired volume, the sample may also be drawn beyond the sample needle 48 to occupy at least a portion of the tubing 56. A desired volume of sample may be drawn into the first fluid channel 64 by accurately controlling the intake stroke of the sample syringe 44. The first fluid channel 64 is "off-line" during the first operational state of the injection valve and therefore is not subject to the high pressure of the system flow which can exceed 7,000 psi. Thus a more complex and costly sample syringe designed to operate under higher system pressure is not required.

FIG. 4B corresponds to the system 60 when the injection valve is in a second operational state as shown, for example, in FIG. 2B. As the injection valve is switched from the first state to the second state, the end of the first fluid channel 64 that was in communication with the sample syringe 44 through node 62C is reconfigured to be in communication with the solvent manager through node 62A and the other end of the first fluid channel 64 that was in communication with the sample source 54 is reconfigured to communicate with the chromatographic column through node 62B. Thus the configuration of the fluid channels 64 and 66 according to the second state means that the flow of mobile phase from the solvent manager is separated (step 220) into two flows, one through each of the fluid channels 64 and 66. The flow rate through each fluid channel 64 and 66 is determined by the flow rate of the mobile phase from the solvent manager and the restriction to flow of each of the fluid channels 64 and 66.

In various embodiments, the second fluid channel 66 provides a predetermined restriction to the flow. For example, the second fluid channel 66 may be a tubing of predetermined diameter and length so that a ratio of the flow rates of the mobile phase through the first and second fluid channels 64 and 66 has a desired value. It should be noted that the flow of mobile phase introduced at one end of the first fluid channel 64 will "push" the previously loaded sample out the opposite end.

At node 62B, the sample that exits the first fluid channel 64 is combined (step 230) with the mobile phase that exits the second fluid channel 66. Thus the combination of the two flows creates a diluted sample. The dilution ratio for the diluted sample is a function of the flow rates in the two fluid channels 64 and 66, therefore a proper selection of the flow restriction provided by the second fluid channel 66 enables a user to obtain a desired dilution ratio anywhere within a wide range of possible dilution ratio values. The injection valve may be maintained in the second state for a predetermined duration such that only a known portion of the volume of the loaded sample is used to generate the diluted sample. Alternatively, the entire volume of loaded sample may be used to generate the diluted sample. Once the entire volume of loaded sample has exited the first fluid channel 64, any subsequent combination of the flows will result in a single flow of the mobile phase without any sample.

Figure 5:
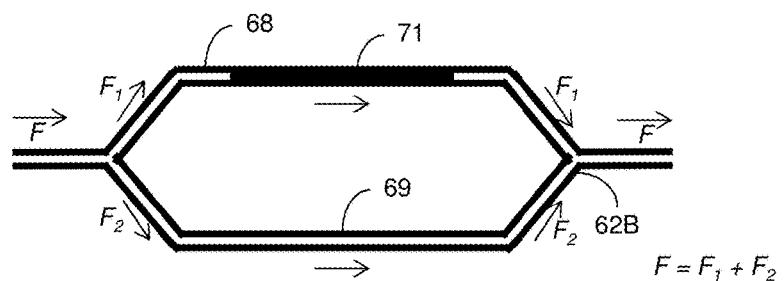
FIG. 5 is a schematic depiction of the use of the two flows of mobile phase to dilute a sample according to embodiments of the invention.

FIG. 5 schematically summarizes the use of the two flows of mobile phase to dilute the sample. The main flow of mobile phase at a flow rate F is separated into a flow in a first fluid channel 68 at a flow rate $F_1$ and another flow in a second fluid channel 69 at a flow rate $F_2$. The flow in the first fluid channel 68 displaces, or "pushes", the loaded sample 71 out the end where it is combined with the flow exiting from the second fluid channel 69 into a single flow at the original flow rate F. It will be understood that the sum of the flow rates $F_1$ and $F_2$ for the two fluid channels 68 and 69 is the same as the flow rate F of the combined flows. If the flow restriction provided by the second fluid channel 69 is decreased so that the flow rate $F_2$ is increased, the dilution ratio is increased. Conversely, if the flow restriction of the second fluid channel 69 is increased, the flow rate $F_2$ is decreased and the dilution ratio is decreased.

It will be appreciated that the dilution ratio is substantially independent of the system flow rate F. More specifically, the dilution ratio is determined according to the ratio of the flow rates $F_1$ and $F_2$, each of which changes proportionately with a change in the main flow rate $F_1$.

Figure 6A:
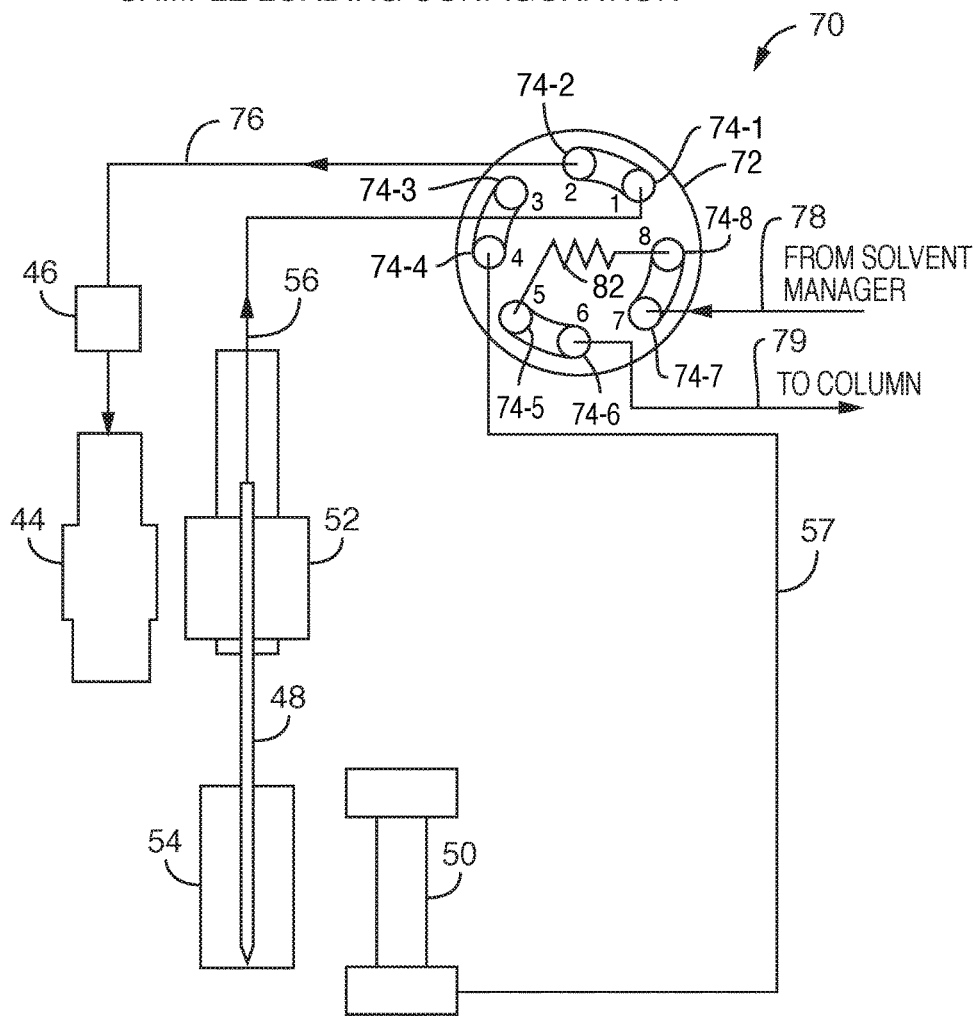
FIG. 6A and FIG. 6B are block diagrams of an embodiment of a system for injecting a diluted sample in a liquid chromatography system. The system includes a rotary shear seal valve shown in a first state and a second state, respectively.
Figure 6B:
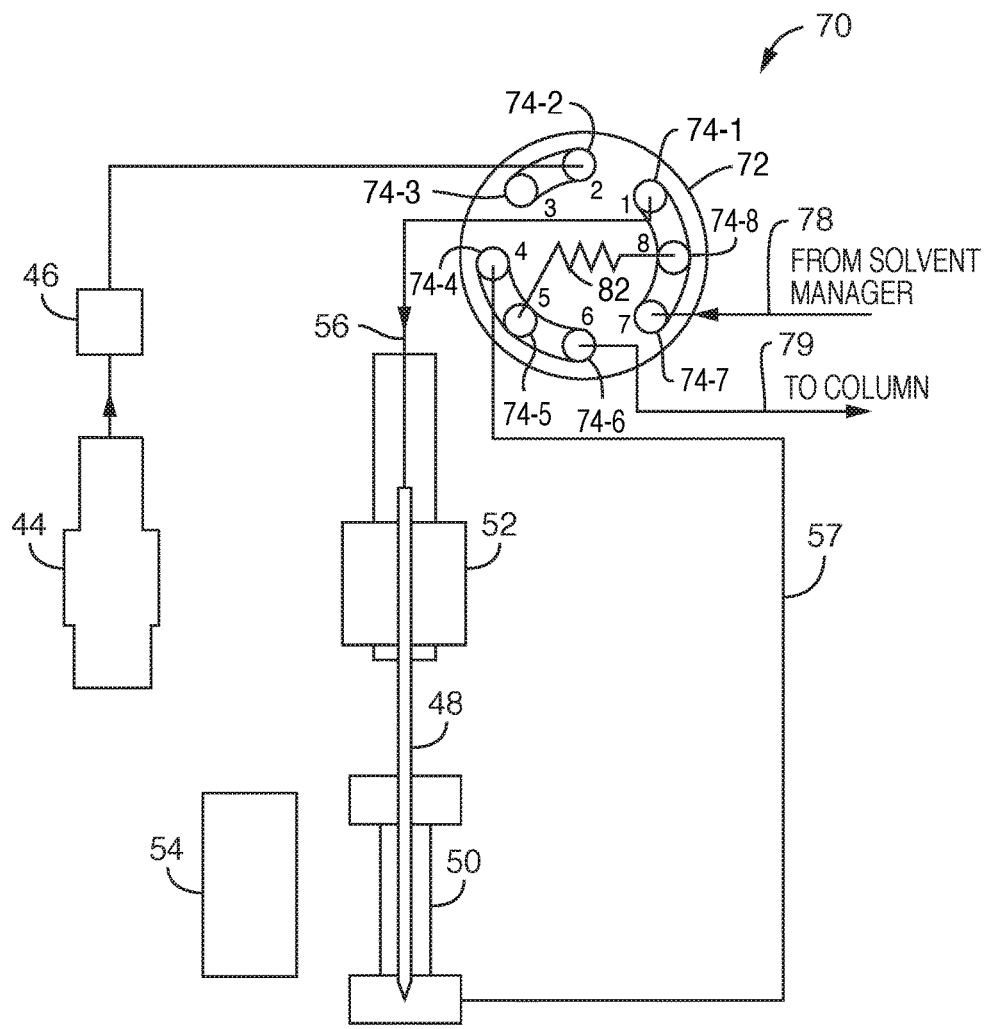

FIGS. 6A and 6B are block diagrams of an embodiment of a system 70 for injecting a diluted sample in a liquid chromatography system similar to the system 40 as shown in FIGS. 2A and 2B, respectively, and each figure shows details of the port configurations for a rotary shear seal injection valve 72. The injection valve 72 includes short fluid paths in the form of grooves in the rotor (shown in shading) and grooves in the stator (shown as clear). The grooves in the rotor move with respect to the ports 74-1 to 74-8 (generally 74) when the injection valve 72 changes states while the grooves in the stator remain stationary with respect to the ports 74 at all times. All ports 74 that are in communication with each other within the injection valve 72 through grooves are considered herein as being at a single node for fluidic communication purposes, as described above with respect to FIGS. 4A and 4B. The injection valve 72 is controlled by a control module (not shown) which may be part of the system processor 12 of FIG. 1 or can be a standalone controller that receives timing or other control signals from a processor.

As illustrated, FIG. 6A shows the system 70 configured for loading the sample into the first fluid channel while the injection valve 72 is in the first state. Tubing 56 that is coupled to the sample needle 48 at one end is coupled to port 74-1 at the other end. The sample syringe 44 and transducer 46 are coupled through tubing 76 to port 74-2. The two ports 74-1 and 74-2 correspond to node 62C in FIG. 4A. Thus sample is drawn from the sample source 54 and liquid is pulled through the injection valve 72 during an intake stroke of the sample syringe 44.

Tubing 78 provides the mobile phase from the solvent manager to port 74-7 and tubing 79 provides the mobile phase leaving the injection valve 72 at port 74-6 to the chromatographic column. The second fluid channel is defined by a flow restrictor 82, such as a length of tubing of known diameter that is coupled at one end to port 74-8 and coupled at the other end to port 74-5. Thus the flow restrictor 82 is an element that is independent of the structure of the injection valve 72. Ports 74-7 and 74-8 are internally coupled and correspond to node 62A of FIG. 4A. Similarly, ports 74-5 and 74-6 are internally coupled and correspond to node 64B of FIG. 4A. Thus mobile phase received at port 74-7 passes through the second fluid channel, as defined by the flow restrictor 82, and exits at port 74-6.

FIG. 6B shows the system 70 configured according to a second state of the injection valve 72. The port couplings remain the same; however, the rotor is rotated to a new position such that the grooves in the rotor are moved in a counterclockwise direction in the figure by one port position. In this second configuration, the mobile phase received at port 74-7 is separated into a first flow and a second flow of mobile phase. The first flow exits at port 74-1 and pushes the loaded sample through the injection port 50 and tubing 57, and into the injection valve 72 at port 74-4. The second flow exits at port 74-8 and passes through the flow restrictor 82 before returning to the injection valve 72 at port 74-5. Grooves in the rotor and stator internally couple ports 74-4, 74-5 and 74-6 as a single node 62B (FIG. 4B). Thus the two flows combine at the node 62B before exiting port 74-6 as a single flow having a diluted sample. The dilution ratio of the diluted sample is a function of the flow rates of the two flows and can be changed between separations by replacing the flow restrictor 82 with another having a different flow restriction. For example, a flow restrictor 82 having a lower flow restriction will pass more mobile phase and therefore result in a greater dilution ratio.

Table 1 provides a non-limiting numerical example of the length and inner diameter (ID) of tubing that can be used for various components in the fluid channels of the illustrated system 70 when configured for a dilution ratio of two. Also shown are the flow rates and pressure drops for the components.

TABLE 1

Dilution Ratio = 2, Mobile Phase Flow Rate = 1 ml/min

| Flow rate | Reference # | Description | Tubing length (in.) | Tubing ID (in.) | Pressure (psi) |
|---|---|---|---|---|---|
| 0.50 | 56 | Needle tubing | 22 | 0.007 | 23.5 |
| 0.50 | 48 | Sample needle | 3.5 | 0.007 | 3.7 |
| 0.50 | 57 | Return tubing | 14.5 | 0.004 | 145 |
| 0.50 | 82 | Flow restrictor | 17.2 | 0.004 | 172.2 |

Table 2 provides another non-limiting numerical example for the components of the system 70 configured for a dilution ratio of three.

TABLE 2

Dilution Ratio = 3, Mobile Phase Flow Rate = 1 ml/min

| Flow rate | Reference # | Description | Tubing length (in.) | Tubing ID (in.) | Pressure (psi) |
|---|---|---|---|---|---|
| 0.33 | 56 | Needle tubing | 22 | 0.007 | 15.5 |
| 0.33 | 48 | Sample needle | 3.5 | 0.007 | 2.5 |
| 0.33 | 57 | Return tubing | 14.5 | 0.004 | 95.8 |
| 0.66 | 82 | Flow restrictor | 8.6 | 0.004 | 113.8 |

Figure 7:
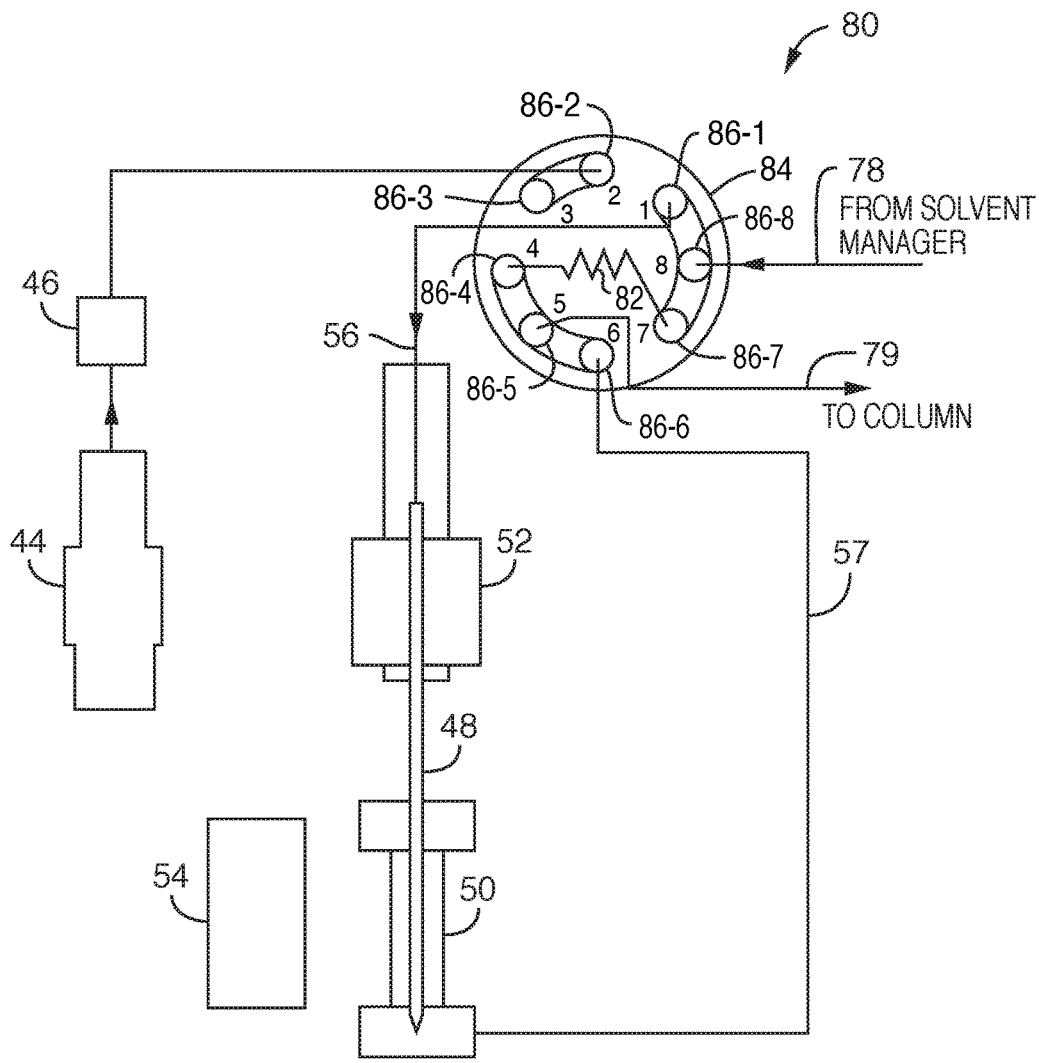
FIG. 7 is a block diagram illustrating another embodiment of a system for injecting a diluted sample in a liquid chromatography system.

FIG. 7 is a block diagram illustrating an alternative embodiment of a system 80 in which an injection valve 84 is used with a different port configuration. The figure represents the injection valve 84 in the second state. The configuration for the injection valve 84 in the first state is not shown; however, it will be recognized that a clockwise change in the depicted rotor position will yield a flow path configuration for sample loading that is similar to the flow paths described above for FIG. 6A.

In the illustrated configuration, the tubing 78 from the solvent manager and the tubing 79 to the chromatographic column are coupled at ports 86-8 and 86-5, respectively. The tubing 56 leading to the sample needle 48 is coupled at port 86-1 and the tubing 57 from the injector port 50 is coupled at port 86-6. The flow restrictor 82 is coupled at one end to port 86-7 and at the other end to port 86-4.

After the injection valve 84 is switched into the illustrated state, the flows of mobile phase and sample are similar to those described above with respect to FIG. 6B. More specifically, the mobile phase received at port 86-8 is separated into a first flow and a second flow of mobile phase. The first flow exits at port 86-1 and pushes the loaded sample through the injection port 50 and into the injection valve 84 at port 86-6. The second flow exits at port 86-7 and passes through the flow restrictor 82 before returning to the injection valve 84 at port 86-4. Grooves in the rotor and stator internally couple ports 86-4, 86-5 and 86-6 as a single node 62B (FIG. 4B). Thus the two flows combine before exiting port 86-5 and passing as a single flow having a diluted sample to the chromatographic column.

Figure 8:
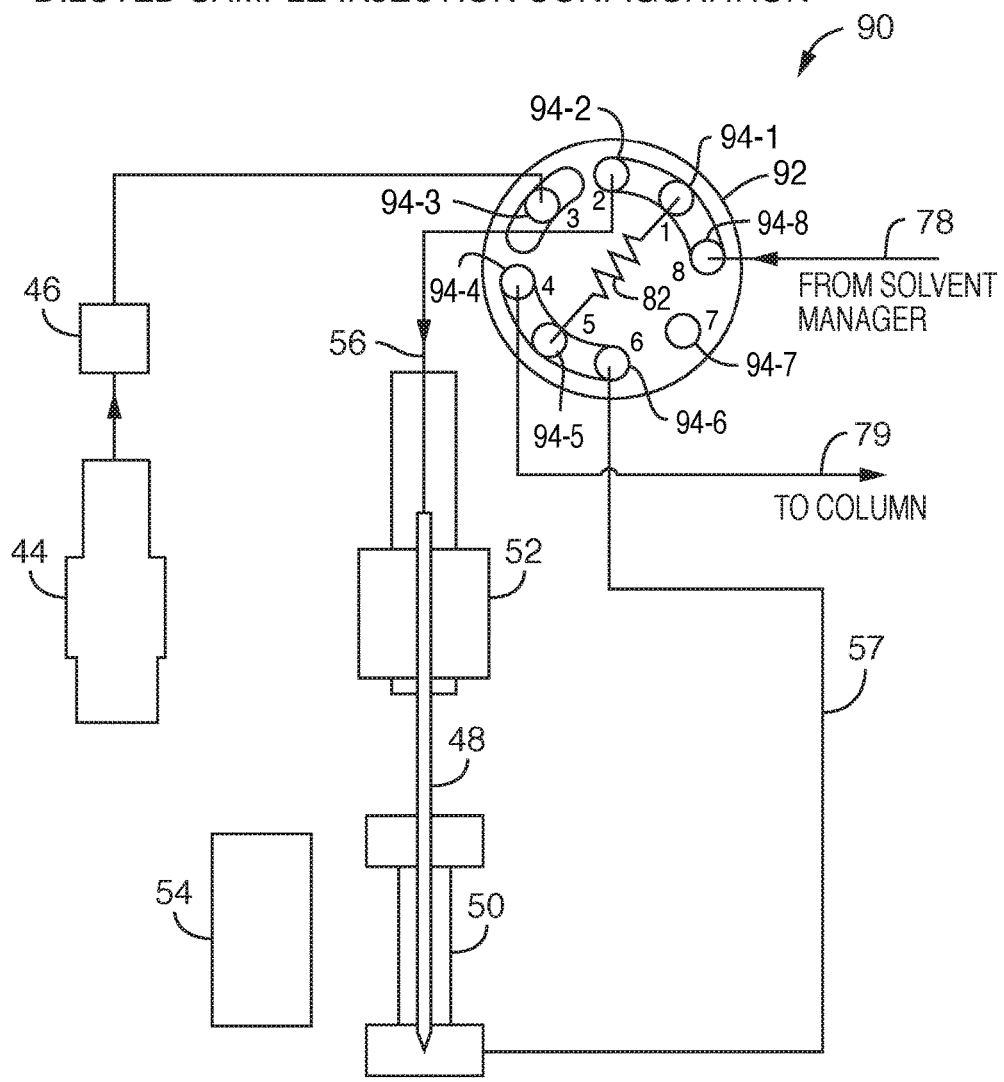
FIG. 8 is a block diagram illustrating another embodiment of a system for injecting a diluted sample in a liquid chromatography system.

FIG. 8 is a block diagram illustrating another embodiment of a system 90 that uses an injection valve 92 having another port configuration. The figure represents the injection valve 92 in the second state. Although the configuration for the injection valve 92 in the first state is not shown, it will be recognized that a clockwise change in the depicted rotor position will yield a flow path configuration for sample loading that is similar to the flow paths described above for FIG. 6A.

The tubing 78 from the solvent manager and the tubing 79 to the chromatographic column are coupled at ports 94-8 and 94-4, respectively. The tubing 56 leading to the sample needle 48 is coupled at port 94-2 and the tubing 57 from the injector port 50 is coupled at port 94-6. The flow restrictor 82 is coupled at one end to port 94-1 and at the other end to port 94-5.

After switching the injection valve 92 into the illustrated state, the flows of mobile phase and sample are similar to those described above with respect to FIG. 6B and FIG. 7. More specifically, the mobile phase received at port 94-8 is separated into a first flow exiting at port 94-2 and a second flow exiting at port 94-1. The first flow pushes the loaded sample through the injection port 50 and into the injection valve 92 at port 94-6. The second flow passes through the flow restrictor 82 before returning to the injection valve at port 94-5. Grooves in the rotor and stator internally couple ports 94-4, 94-5 and 94-6 as a single node 62B (FIG. 4B). Thus the two flows combine before exiting port 94-4 and passing as a single flow with the diluted sample to the chromatographic column.

While the invention has been shown and described with reference to specific embodiments, it should be understood by those skilled in the art that various changes in form and detail may be made therein without departing from the spirit and scope of the invention as recited in the accompanying claims.

What is claimed is:

1. A method of diluting a sample in a liquid chromatography system, the method comprising:
   loading a sample into a first fluid channel;
   separating a flow of a mobile phase of a liquid chromatography system at a valve into a first flow in the first fluid channel and a second flow in a second fluid channel, the first flow and the second flow having a first flow rate and a second flow rate, respectively, wherein the flow of mobile phase in the first fluid channel displaces the sample in the first fluid channel; and
   combining the sample exiting the first fluid channel and the mobile phase exiting the second fluid channel at a location of injection into the system flow to thereby generate a diluted sample in the system flow, wherein a dilution ratio of the diluted sample is responsive to the first flow rate and the second flow rate.

2. The method of claim 1 wherein loading a sample comprises drawing the sample from a sample source into the first fluid channel with a sample syringe.

3. The method of claim 1 wherein the sample loaded into the first fluid channel includes a sample in a diluent.

4. The method of claim 1 wherein the sample exiting the first fluid channel and the mobile phase exiting the second fluid channel are combined for a predetermined duration.

5. The method of claim 1 wherein only a portion of a volume of the sample loaded into the first fluid channel is combined with the mobile phase exiting the second fluid channel to generate the diluted sample.

6. A system for injecting a diluted sample in a liquid chromatography system, comprising:
   a first fluid channel having a first end and a second end;
   a second fluid channel having a first end and a second end;
   an injection valve having a first node and a second node in communication with the first end and the second end, respectively, of the second fluid channel, and having a third node configured for communication with a sample syringe, the first node configured to receive a mobile phase of a liquid chromatography system; and a control module in communication with the injection valve to control a state of the injection valve, wherein, when the injection valve is in a first state, the third node is in communication with the first end of the first fluid channel to thereby enable a sample in a sample source in communication with the second end of the first fluid channel to be loaded into the first fluid channel, wherein, when the injection valve is in a second state, the first node is in further communication with the first end of the first fluid channel and the second node is in further communication with the second end of the first fluid channel so that the mobile phase flows into the first fluid channel and the second fluid channel, at a first flow rate and a second flow rate, respectively, and wherein the sample displaced out from the second end of the first fluid channel and the mobile phase exiting the second end of the second fluid channel are combined at the second node to generate a flow of a diluted sample having a dilution ratio that is responsive to the first flow rate and the second flow rate.

7. The system of claim 6 further comprising a sample source in communication with the second end of the first fluid channel.

8. The system of claim 6 further comprising a sample syringe in communication with the third node of the injection valve.

9. The system of claim 6 wherein each of the nodes comprises at least one injector port.

10. The system of claim 6 wherein at least one of the nodes of the injector ports comprises a plurality of ports in communication with each other through at least one fluid channel in the injection valve.

11. The system of claim 6 wherein the injection valve is a rotary shear seal valve.

12. The system of claim 11 wherein at least one of the nodes of the injector ports comprises a plurality of ports in communication with each other through at least one fluid channel in the rotary shear seal valve.

13. The system of claim 12 wherein the at least one fluid channel in the rotary shear seal valve includes a groove in a rotor or a stator.

14. The system of claim 12 wherein the sample in the sample source includes a sample in a diluent.

* * * * *